(12) United States Patent
Durkop et al.

(10) Patent No.: US 7,052,864 B2
(45) Date of Patent: May 30, 2006

(54) BIOANALYTICAL MEASURING METHOD USING OXIDASES AND LANTHANOID-LIGAND COMPLEXES

(75) Inventors: Axel Durkop, Regensburg (DE); Otto Wolfbeis, Regensburg (DE)

(73) Assignee: Active Motif Chromeon GmbH, Tegernheim (DE)

( * ) Notice: Subject to any disclaimer, the term of this patent is extended or adjusted under 35 U.S.C. 154(b) by 456 days.

(21) Appl. No.: 10/093,103

(22) Filed: Mar. 8, 2002

(65) Prior Publication Data

US 2002/0137027 A1   Sep. 26, 2002

(30) Foreign Application Priority Data

Mar. 9, 2001   (DE) ................. 101 11 392

(51) Int. Cl.
*C12Q 1/26* (2006.01)
*C12Q 1/54* (2006.01)
*C12Q 1/68* (2006.01)
*G01N 33/533* (2006.01)

(52) U.S. Cl. ............... 435/25; 435/6; 435/11; 435/14; 436/546; 436/172; 436/164

(58) Field of Classification Search ............ 435/6, 435/11, 14, 25; 436/546, 164, 172
See application file for complete search history.

(56) References Cited

U.S. PATENT DOCUMENTS 5,262,299 A * 11/1993 Evangelista et al. ........... 435/6

FOREIGN PATENT DOCUMENTS

DE   198 13 247 C1   6/1999
WO   WO 94 02486 A1   2/1994

OTHER PUBLICATIONS

Rakicioglu et al., "Increased luminescence of the tetracycline-europium (III) system following oxidation by hydrogen peroxide", Journal of Pharmaceutical and Biomedical Analysis, vol. 20, No. 1-2, Jun. 1999, pp. 397-399.

Saiki et al., "Use of tetracycline as complexing agent in radiochemical separations", Journal of Radioanalytical Chemistry, vol. 64, No. 1-2, 1981, pp. 83-116.

Hadi et al., Complexation of some antibiotics with lanthanum (III), EGYPT. J. Chem., vol. 39, No. 1, 1996, pp. 49-58.

* cited by examiner

*Primary Examiner*—Mary E. Ceperley
(74) *Attorney, Agent, or Firm*—Rothwell, Figg, Ernst & Manbeck

(57) ABSTRACT

The present invention concerns biological methods of determination using enzymes from the group of oxidases and using optical indicators from the group of lanthanoid-ligand complexes.

26 Claims, 10 Drawing Sheets

BIOANALYTICAL MEASURING METHOD USING OXIDASES AND LANTHANOID-LIGAND COMPLEXES

The present invention concerns biological methods of determination using enzymes from the oxidase group and using optical indicators from the group of lanthanoid-ligand complexes.

Enzymatic methods play an important role in bioanalytics. Important questions are for example the determination of the presence of a certain enzyme or the quantitative determination of the activity of enzymes. Substrates which are converted by enzymes can also be detected or determined by enzymatic methods. Methods which are often carried out for example include the detection and determination of substrates such as glucose, alcohol, cholesterol and triglycerides. Finally it is also possible to detect or determine inhibitors or activators of enzymes by quantitatively measuring their retarding or accelerating effect on the reactions. A summary is given in *Enzymatic Methods of Analysis,* G. G. Guilbault, Pergamon Press, 1970.

Two types of enzymes are preferably used for enzymatic methods, dehydrogenases and oxidases. Dehydrogenases for example form NADH from $NAD^+$ which can be detected by means of its characteristic absorption at 345 nm or by means of its fluorescence at 455 nm.

The activity of oxidases which consume oxygen and form hydrogen peroxide can for example be detected by measuring the consumption of oxygen or the formation of $H_2O_2$.

Glucose oxidase is an example of an enzyme which can be used in a method of determination using oxidases which converts glucose into gluconic acid lactone and an equimolar amount of $H_2O_2$. Hence glucose (e.g. in blood or in drinks) or other substrates of oxidases can be quantified via the determination of $H_2O_2$. Oxidases can for example also be used as markers in enzyme tests or to detect a formed antigen-antibody complex (which then also contains glucose oxidase) (e.g. in immunological tests of the sandwich assay type). A hybridization reaction between two nucleic acid strands can be detected in a corresponding manner.

At present various enzymatic methods are used, for example electrometric methods of determination for oxidases and substrates thereof. Vadgama et al., describe an electrochemical sensor for determining reaction products of oxidases. It is based on the use of a permeation-selective medium and on the electrochemical detection of the generated hydrogen peroxide (EP 503 943). An electrochemical-enzymatic method is also described in WO 9953301 which, however, is based on the use of 2 electrodes (with different membranes). Amperometric glucose measuring instruments are commercially available.

Recently optical methods such as for example absorptiometric and reflection methods for the determination of oxidases and their substrates have been the focus of particular interest since they have the capability of being more simple and above all more specific. Optical methods are usually based on an irreversible chemical reaction between the hydrogen peroxide formed by oxidases and a colourless initial substance (e.g. dianisidine) which results in a strongly coloured product whose colour intensity can be measured and related to the amount present of enzyme or substrate.

Genovesi et al. report a photometric colour test for glucose (*Proc. SPIE-Int. Soc. Opt. Eng.* 990 (1989) 22–28). A so-called test strip is also described in U.S. Pat. No. 5,281,395. Biosensors are described in WO 9805424 which are based on the determination of enzyme substrates by means of an irreversible colour reaction.

Some of these methods are used commercially in so-called test strips which are analysed by reflectometry. However, a disadvantage of the said optical methods is that the resulting dyes are unstable, hence the result can be falsified (*Clin. Chem.* 19 (1973) 1227–8).

Matsubara et al., report that oxo[5,10,15,20-tetra(4-pyridyl)porphyrinato]titanium (IV) complexes form a yellow complex with an absorption maximum at 432 nm with urea in the presence of the enzyme uricase which is suitable for the quantitative photometric (but not fluorimetric) determination of uric acid (*J. Pharmaceutical Soc. Jap.* 114 (1994) 48–53).

Other optical methods are chemiluminescent methods of determination for oxidases. Chemiluminescence is understood as the emission associated with a chemical reaction of visible, ultraviolet or possibly infrared light below the annealing temperature of the substances involved. A chemiluminescent method for example utilizes the fact that hydrogen peroxide formed by oxidases reacts with reagents such as luminol (G. L. Kok, T. P. Holler, M. B. Lopez, H. A. Nachtrieb, M. Yuan, *Environm. Sci. Technol.* 1978, 12, 1072; T. M. Freeman, W. R. Seitz, *Anal. Chem.* 1978, 50, 1242) or peroxalates (P. van Zoomen et al., *Anal. Chim. Acta* 1985, 167, 249) with emission of a green or blue chemiluminescence (M. A. DeLuca, W. D. McElroy, (eds.) *Bioluminescence & Chemiluminescence,* Academic Press, New York, 1981). It is also known that divalent europium complexes emit chemiluminescence when they are treated with oxidizing agents (Elbanowski et al., *Photochem. Photobiol.* 47 (1988) 463–6; Elbanowski et al., *J. Alloys Compd.* 275–277 (1998) 225–229). However, the chemiluminescence effect in this case is only observable while the reagent is present. Hence methods based on the measurement of chemiluminescence advantageously do not require a light excitation source, but have the disadvantage that the light-emitting species (e.g. luminol) is consumed by a chemical reaction over time.

Fluorescent methods of determination are also used for oxidases. The status of fluorescent-analytical techniques is described in *J. Biomed. Opt.* 5 (2000) 5–16 and WO 0011205.

Weber et al., report in WO 0002048 on an optical sensor for the in situ measurement of analytes with particular emphasis on the analysis of glucose. Other analytical methods for glucose are described in WO 9855869. A microfibre optical arrangement for the fluorescent enzymatic determination of glucose by measuring oxygen consumption is described in U.S. Pat. No. 6,157,442.

Chua et al., report on a method for measuring plasma glucose (*Clin. Chem.* 24 (1978) 150–2) and Tolosa et al. describe an optical method based on luminescence (*Sens. Actuators.* B. 45 (1997) 93–99). A fluorescent method is described in *Biosensors & Bioelectron.* 15 (2000) 69–76 which also measures oxygen consumption by the enzyme.

Other fluorescence-optical methods are for example based on the irreversible oxidation of phenols to fluorescent dimers in the presence of peroxidase (*Anal. Chim. Acta* 1986, 186, 131) or of manganese salts (*Talanta* 1986, 33, 914). The resulting reaction products have to be excited with UV light (which is not necessary in chemiluminescent methods) in order to then emit a light blue fluorescence. Zhou et al., describe a reaction with a derivative of the dye resorufin which forms a green fluorescent product when reacted with hydrogen peroxide (*Anal. Biochem.* 253 (1997) 162–168).

The hydrogen peroxide formed in enzymatic reactions can also be detected by reacting it with p-hydroxyphenylcarboxylic acids (e.g. p-hydroxybenzoic acid or homovanillic acid) under the influence of peroxidase. A dimer is formed in this process which strongly fluoresces at 315 nm under UV excitation (with a maximum at ca. 415 nm), (*Sensors & Actuators* B28 (1995) 3–7). A disadvantage is that all biological materials have a strong interfering self-fluorescence when excited at 315 nm. Hence all methods based on the formation of fluorescent products that are excited by UV light are strongly interfered with by the fluorescence of biological materials.

The sensitivity and selectivity of the method using homovanillic acid can be increased by reacting the dimer formed by hydrogen peroxide with europium(Eu) (III) ions to form a more readily detectable chelate (*Analyst* 122 (1997) 455). The selectivity of this method is based on the fact that the slow decay time of the fluorescence of the Eu chelate can be utilized to control the measurement process in such a manner that the rapidly decaying background fluorescence of the sample is firstly allowed to decay and only afterwards is the spectrally clearly separated fluorescence of the chelate measured which is hence very specific. A method for determining glucose using the enzyme horseradish peroxidase and glucose oxidase and the reagents p-hydroxyphenylpropionic acid and Tb(EDTA) is described in DE 198 13 247.6. The decay of this fluorescence is also considerably slower than that of the background fluorescence of many biological samples.

This method was described in more detail in *Analyst* 125 (2000) 1537–1538. Oxidase substrates were determined by adding the oxidase as the first reagent to the test solution followed by p-hydroxyphenylpropionic acid (pHPPS) as the second reagent and the enzyme peroxidase as the third reagent. The hydrogen peroxide formed by the oxidase reacts under the influence of peroxidase with pHPPS to form a dimer that forms a luminescent complex with the $4^{th}$ reagent (a lanthanide ion) the fluorescence of which is amplified by addition of the $5^{th}$ reagent (caesium chloride). These methods are indeed sensitive but irreversible and very laborious due to the need for 5 reagents.

The previously described enzymatic methods have the disadvantages that they (a) either have to be carried photometrically which is very difficult in strongly coloured solutions or (b) the background fluorescence is so strong that all other signals are masked or (c) the measurement is only indirect (i.e. via measurement of oxygen consumption). A disadvantage of the latter is that the oxygen partial pressure is often unknown or varies during the measurement or from sample to sample. The object of the present invention was to provide a method which at least partially eliminates the disadvantages of the prior art.

The object of the invention was achieved by providing a method for determining enzymatically generated hydrogen peroxide characterized in that hydrogen peroxide which is formed by an enzyme selected from the group of hydrogen peroxide-generating oxidases is determined with the aid of a lanthanoid-ligand complex.

It was surprisingly found that the absorption as well as the luminescence of suitable present lanthanoid-ligand complexes is changed during the catalytic activity of oxidases.

Hence it is possible to determine an activity of at least one enzyme selected from the group of hydrogen peroxide-generating oxidases by determining the generated hydrogen peroxide with the aid of a lanthanoid-ligand complex.

The hydrogen peroxide released by oxidases results in a change in the optical and in particular in the luminescence-optical properties of indicator substances such as lanthanoid-ligand complexes and can be detected or quantitatively determined with the aid of the lanthanoid-ligand complex.

This for example enables enzymes, enzyme activities, enzyme substrates, enzyme inhibitors or enzyme activators to be detected or determined in an improved manner. Furthermore antigens and nucleic acid oligomers can also be detected or determined by using oxidases as markers e.g. in immunological or genetic test methods.

Oxidases refers to enzymes from the group of oxidoreductases, which lead to redox reactions with molecular oxygen as the electron acceptor. If four electrons are transferred to oxygen, then water or carbon dioxide is formed, if two electrons are transferred hydrogen peroxide ($H_2O_2$) is formed.

"Hydrogen peroxide-generating oxidases" are all enzymes from the oxidoreductase group which oxide their substrate with consumption of oxygen and formation of hydrogen peroxide. Examples of oxidases that are preferable used in the method according to the invention are glucose oxidase, galactose oxidase, cholesterol oxidase, sarcosine oxidase, xanthine oxidase, bilirubin oxidase, amine oxidase, amino acid oxidase, alcohol oxidase, lactate oxidase, pyruvate oxidase and uricase.

The present invention discloses a new method for the simple determination of the activity of hydrogen peroxide-generating oxidases and the concentration of biomolecules by using a lanthanoid-ligand complex. In contrast to methods that are described in the prior art, the method according to the invention advantageously only requires one additional reagent apart from the oxidase i.e. the lanthanoid-ligand complex. The method according to the invention enables a qualitative or quantitative determination to be carried out. For example enzymes, enzyme activities, enzyme substrates, enzyme inhibitors, enzyme activators, antigens or nucleic acid oligomers can be determined.

The determination can for example be carried out in biological tissue, in microbial or viral cultures or in wells of microtitre plates.

The enzyme from the oxidase group can be present in the method according to the invention in a free form, as an oxidase-labelled antibody or as an oxidase-labelled oligonucleic acid.

Hence the present invention encompasses qualitative optical detection methods and quantitative optical methods of determination for enzyme activities, enzyme substrates, enzyme inhibitors, enzyme activators, antigens or nucleic acid oligomers using at least one enzyme from the oxidase group characterized in that the hydrogen peroxide formed by oxidases, by oxidase-labelled antibodies or by oxidase-labelled oligonucleic acids is detected during their enzymatic activity with the aid of a reagent composed of a trivalent lanthanoid ion, preferably an ion of the elements europium, terbium, holmium, dysprosium, erbium or samarium and an organic ligand, in which the hydrogen peroxide results in a measurable change in the optical properties of the reagent the magnitude of which can for example have a known or previously determined relationship to the concentration of the enzyme, enzyme substrate, enzyme inhibitor, antigen or oligomer to be determined.

In a preferred embodiment of the method according to the invention enzyme activities are determined by degrading a substrate in several steps by enzymes of which at least one belongs to the group of oxidases and the resulting formation of hydrogen peroxide is detected or determined with the aid of a lanthanoid-ligand complex and this is used to determine the enzyme activity of the first enzyme in the enzyme cascade.

The method according to the invention can for example be used to detect or determine the activity of oxidases. Oxidases are enzymes which oxidize oxygen as a second substrate and produce hydrogen peroxide. In the enzyme catalogue (E.C.) they have the number 1.X.3 whereby the number 1 indicates that it is an enzyme from the group of oxidoreductases, the number X represents the respective substrate group and the number 3 indicates that it is an oxidase. Oxidases from the substrate groups 1 to 14 are frequently determined or detected.

A preferred embodiment of the invention for determining the activity of oxidases is characterized in that an added substrate is degraded by the oxidase and the resulting formation of hydrogen peroxide is detected or determined with the aid of a lanthanoid-ligand complex and is used to determine the activity of the oxidase. In a further embodiment the activity of an enzyme can be determined by degrading a substrate in several steps by enzymes of which at least one belongs to the group of oxidases and determining the resulting formation of hydrogen peroxide with the aid of a lanthanoid-ligand complex which is used to determine the enzyme activity of the first enzyme in the enzyme cascade.

In order to detect the presence of an enzyme according to the invention a lanthanoid-ligand complex is firstly added and subsequently the corresponding enzyme substrate. Then the fluorescence is excited at a wavelength of preferably 330 to 415 nm and the emission intensity is detected at ca. 600 to 630 nm. FIG. 5 shows an example of how the enzyme activity of the enzymes glucose oxidase and galactose oxidase can be detected in the wells of microtitre plates by adding a lanthanoid-ligand complex and substrate and subsequent fluorometric measurement of the microtitre plate.

A further preferred embodiment of the method according to the invention is the determination of enzyme substrates.

Substrates are preferably determined from the group of oxidases. Oxidases refers to enzymes from the oxidoreductase group which accept oxygen as a second substrate. Oxidases oxidize their substrate with consumption of oxygen and formation of hydrogen peroxide.

Suitable oxidases for this embodiment of the present invention are for example glucose oxidase, galactose oxidase, cholesterol oxidase, sarcosine oxidase, xanthine oxidase, amine oxidase, amino acid oxidase, alcohol oxidase, lactate oxidase, pyruvate oxidase or uricase. In addition it is also possible to use any hydrogen peroxide-generating oxidases. The method according to the invention can be used to determine substrates which are directly converted by oxidases. Examples of such substrates are glucose, lactate, cholesterol, bilirubin or alcohol. For example the substrate glucose (blood sugar) is oxidized by the enzyme glucose oxidase according to the following reaction equation:

$$C_6H_{12}O_6 + O_2 \rightarrow C_6H_{10}O_6 + H_2O_2$$

(glucose+oxygen→gluconic acid lactone+hydrogen peroxide).

One molecule of hydrogen peroxide is formed per converted molecule of glucose. Hence glucose can be determined by measuring the amount of hydrogen peroxide that is formed. The determination can for example be carried out kinetically which means that the kinetics of the formation of hydrogen peroxide is monitored over time and preferably over a period of 1 to 5 minutes.

The lanthanoid-ligand complexes according to the invention have proven suitable for the bioanalysis of substrates of oxidases. FIG. 6 shows a change in the emission over time as a function of the glucose concentration present in a sample. A plot of the change of emission per time unit 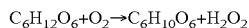 against the glucose concentration shows that glucose can be quantitatively determined with the method according to the invention in a concentration range preferably between 2 and 50 mMol/l. This is shown in FIG. 7.

Examples of the determination of enzyme substrates with the method according to the invention are the determination or detection of glucose in blood, serum, saliva, interstitial fluid, alcoholic or non-alcoholic drinks (or precursors thereof) or in bioreactors using glucose oxidase.

Lactate oxidase can for example be used in the method according to the invention to detect or determine the substrate lactate in blood, serum, interstitial fluid or in bioreactors. In addition it is also possible to determine the substrates cholesterol or bilirubin in blood or serum using cholesterol oxidase or bilirubin oxidase.

Alcohol in blood, saliva, serum, interstitial fluid, alcoholic or non-alcoholic drinks (or precursors thereof) or in bioreactors can also be determined with the aid of the method according to the invention for determining enzyme substrates by using alcohol oxidase.

Substrates which are not directly converted by oxidases can also be determined by the method according to the invention using lanthanoid-ligand complexes. In this case the substrate is firstly converted by one or several non-oxidases into a product which is in turn a substrate for an oxidase and which can be further converted by it to form hydrogen peroxide. An example of an enzyme cascade of this type is shown in the following for the clinically significant substance creatinine:

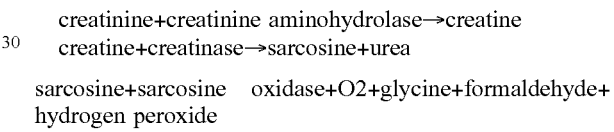

sarcosine+sarcosine oxidase+O2+glycine+formaldehyde+hydrogen peroxide

Hence the present invention also encompasses a method for detecting or determining an enzyme substrate wherein the substrate to be determined is firstly converted by at least one enzyme which does not belong to the class of oxidases and the last product of this enzyme cascade is converted by an oxidase. An example of this is an embodiment in which the first enzyme of the enzyme cascade is creatinine amidohydrolase, the second enzyme of the enzyme cascade is creatinase and the third enzyme of the enzyme cascade is sarcosine oxidase whereby the method can be used to detect or quantitatively determine creatinine in body fluids.

The method according to the invention for determining creatinine is advantageously easier to handle, detect and quantify since, in contrast to the methods described in the prior art (Goren et al., Clinical Chemistry 32 (1986) pages 548 to 551) no other enzymes such as peroxidase or reagents such as anisidine, aminoantipyrine or 2,4,6-tribromo-3-hydroxybenzoic acid have to be added apart from the lanthanoid-ligand complex.

The present invention also encompasses a method for detecting or quantitatively determining enzyme inhibitors in which the reaction-retarding effect of an enzyme inhibitor on the degradation of an enzyme substrate by an oxidase with release of hydrogen peroxide is detected or quantitatively determined with the aid of the lanthanoid-ligand complex.

A further subject matter of the present invention is a method for the detection or quantitative determination of enzyme inhibitors in which the reaction-retarding effect of an enzyme inhibitor on the degradation of an enzyme substrate and release of hydrogen peroxide caused by one or several enzymes of which at least one is from the group of oxidases is detected or quantitatively determined with the aid of a lanthanoid-ligand complex and is used to detect or determine the enzyme inhibitor of the first enzyme of the enzyme cascade. The first enzyme of such an enzyme cascade is preferably a protease or peptidase.

The method according to the invention for determining enzyme inhibitors can for example be used to screen the effectiveness of potential enzyme-inhibiting substances. Such a screening is for example suitable for finding potential pharmacological agents. The enzyme inhibitor can also be a toxic substance and the method according to the invention can be used to detect or quantitatively determine toxic substances in biological samples, in foods or in environmental samples.

The present invention also concerns a method for detecting or quantitatively determining enzyme activators in which the reaction-accelerating effect of an enzyme activator on the degradation of an enzyme substrate by an oxidase with release of hydrogen peroxide is detected or quantitatively determined with the aid of a lanthanoid-ligand complex.

Enzyme activators that can be determined with the aid of the method according to the invention are for example monovalent or divalent metal ions.

In a further embodiment the method according to the invention is used to detect or quantitatively determine enzyme activators wherein the reaction-accelerating effect on the degradation of an enzyme substrate or release of hydrogen peroxide caused by one or several enzymes of which at least one is from the group of oxidases is detected or quantitatively determined with the aid of a lanthanoid-ligand complex and is used for the detection or determination of the enzyme activator of the first enzyme of the enzyme cascade.

A further preferred embodiment of the present invention concerns a method for the detection or quantitative determination of antigens. Suitable oxidases such as glucose oxidase or galactose oxidase can be used as markers in optical immunoassays. Typically an antibody is labelled with an oxidase (labelled with * in the following). If the antibody labelled in this manner (*AB) now finds a corresponding antigen (AG), an *AB-AG complex is formed which also includes the oxidase and can be detected by means of its activity (Papkovsky et al., *Anal. Chem.* 71 (1999) pages 1568–1573). In one of the methods for determining the activity of glucose oxidase that is described in the prior art, an oxygen sensor is used and the oxygen consumption caused by the enzymatic activity is measured. This method is only accurate when the oxygen content of the sample and standard are equal. However, this cannot always be ensured.

With the aid of the lanthanoid-ligand complexes according to the invention which are used as indicators for hydrogen peroxide it is now for the first time possible to directly detect the formation of hydrogen peroxide in immunoassays of the ELISA type and advantageously also with variable oxygen saturation.

Hence the present invention also concerns a method for detecting or quantitatively determining antigens in which an oxidase-labelled antibody is used in an immunoanalytical method and, after single or multiple antigen-antibody binding and addition of enzyme substrate, the hydrogen peroxide formed by the oxidase is detected or determined and used for the detection or determination of the antigen.

The present invention also encompasses a method for the detection or quantitative determination of antigens in which a sandwich assay or an ELISA is carried out. The determination or detection of antigens can for example be carried out in blood, serum, saliva, interstitial fluid, alcoholic or non-alcoholic drinks (or precursors thereof), in environmental samples or in bioreactors. In addition an immunohistochemical detection of antigens can be carried out in which an oxidase-labelled antibody binds to an antigen in a tissue section and the site of binding is visualised by adding a lanthanoid-ligand complex and an enzyme substrate and preferably it is optically made visible with the aid of a microscope.

In a further preferred embodiment of the method according to the invention nucleic acid oligomers are detected or quantitatively determined by means of hybridization assays. Hybridization assays are of major importance for the detection of genetically modified DNA. A detection of genetically modified DNA can for example be desirable in medical diagnoses, in forensic analyses or to detect genetically modified foods. In hybridization assays the occurrence (or absence) of double-strand formation from two complementary or non-complementary single strands is detected. In complex samples it is not possible to detect hybridization photometrically or only by using complicated technical apparatus which is why fluorescent labelling methods are used for the detection.

By labelling a DNA or a partial strand of a DNA with an oxidase it is possible, like an immunoassay, to detect a hybridization by detecting the hydrogen peroxide formed as a result of the enzymatic activity by means of lanthanoid-ligand complexes. For example in a preferred embodiment of the method according to the invention an amino-modified oligomer is labelled with an oxidase. When this first labelled oligomer (Oli-1) meets its corresponding counterpiece (Oli-2) a duplex is formed which also contains the oxidase and can be detected via the activity of the oxidase.

The present invention also concerns a method for the detection or quantitative determination of nucleic acid oligomers in which a nucleic acid single strand is labelled with an oxidase and its activity is detected by means of the generated hydrogen peroxide after hybridization or re-hybridization and after addition of enzyme substrate and is used to detect or quantitatively determine a nucleic acid sequence. The oxidases glucose oxidase or galactose oxidase are preferably used to detect or quantitatively determine nucleic acid oligomers.

Nucleic acid oligomers can for example be determined in blood, sperm, saliva, foods, plants or seed material, genetic material, bacteria, viruses or bioreactors.

In the method of the present invention the oxidase can be present as a free oxidase, as an oxidase-labelled antibody or as an oxidase-labelled oligomer in a dissolved form in the solution to be determined and/or the lanthanoid-ligand complex can be used in a dissolved form.

The oxidase, the oxidase-labelled antibody or the oxidase-labelled oligomer and/or the lanthanoid-ligand complex can also be present in an immobilized form; for example immobilized on planar elements such as the bottom of a microtitre plate, on or in particles or on a light guide preferably a fibre-optical light guide where the immobilized oxidase is preferably in direct contact with the sample to be determined. Immobilization can be achieved by any known system and preferably the streptavidin-biotin or the avidin-biotin system is used for the immobilization.

One embodiment of the method is characterized in that the oxidase, oxidase-labelled antibody or oxidase-labelled oligomer and the lanthanoid-ligand complex is present in a dissolved form in a well of a microtitre plate together with the sample to be examined and the change in the optical properties of the lanthanoid-ligand complex is measured by a microtitre plate reader or by imaging methods preferably fluorescent imaging methods. In another embodiment the lanthanoid-ligand complex and/or oxidase, oxidase-labelled antibody or oxidase-labelled oligomer are present in an immobilized form in the wells of the microtitre plate and the change in the optical properties is determined by a microplate reader or by means of fluorescent imaging methods.

When particles are used for the immobilization, the oxidase, oxidase-labelled antibody or oxidase-labelled oligomer and/or lanthanoid-ligand complex can be immobilized in or on the particles. The particles can be labelled by any suitable labelling method, preferably by fluorescent labelling. The particles can also have a magnetic core.

Suitable particles have a diameter of 0.1 to 20 µm, more preferably 0.1 to 10 µm and most preferably of 1 to 5 µm.

The particles can be used in heterogeneous immunoassays or gene tests or in flow-cytometric detection methods.

In a preferred embodiment of the method according to the invention a flow system is used which includes a mechanical feed of sample material, solvent and/or enzymes, enzyme-labelled antibodies or enzyme-labelled oligomers and/or the lanthanoid-ligand complex. In one embodiment of the method a flow system is used in which the sample material and solvent are delivered mechanically, and the lanthanoid-ligand complex and/or enzyme, enzyme-labelled antibody, or enzyme-labelled oligomer are either conveyed by the flow system or are present in an immobilized form.

The method according to the invention can also be carried out when the lanthanoid-ligand complex, the enzyme or both are not present in solution but are immobilized for example in a biosensor. The lanthanoid-ligand complex and/or the oxidase can for example be embedded in and/or immobilized on the surface of a polymer membrane. Suitable polymers retain the lanthanoid-ligand complex and the enzyme in such a manner that they are not washed out and allow the enzyme substrate to diffuse in so that binding can occur in the interior of the membrane.

Thin polymer layers are for example used in the prior art in irreversible colour tests and are referred to as test strips (Sonntag, "Trockenchemie: Analytik mit Träger-gebundenen Reagenzien", Thieme Publishers, Stuttgart, 1988). Such thin layers have the advantage that they allow the examination of optically non-transparent samples (e.g. blood) since the intrinsic colour of the sample no longer interferes in contrast to tests in liquid solution where it is not possible to examine strongly coloured test materials due to the self-absorption of the sample material.

In a further embodiment of the method according to the invention the oxidase, oxidase-labelled antibody or oxidase-labelled oligomer and/or the lanthanoid-ligand complex can be present in an immobilized form in or on a polymer matrix and come into contact with the sample to be examined.

The polymer matrix used in the method according to the invention is preferably permeable to hydrogen peroxide, has a thickness of 0.05 to 20 µm, preferably of 0.1 to 10 µm and can for example be used as a biosensor in disposable tests or be used several times in succession. Suitable polymer matrices are composed of a hydrogel and the lanthanoid-ligand complex can be present physically or chemically immobilized in the polymer matrix.

In one embodiment of a sensor membrane a single sensor layer (for example consisting of a hydrogel with EuTc and glucose oxidase contained therein) is disposed on an inert but optically transparent polyester layer. In another embodiment the biosensor consists of two layers, namely one layer made of a hydrogel with the lanthanoid-ligand complex contained therein and a second layer layered thereon consisting of glucose oxidase immobilized on a support (e.g. a nylon net). The fluorescence of the EuTc can be scanned from the polyester side by irradiating it for example at an excitation wavelength $\lambda ex$ of 405 nm and measuring the emission for example at a wavelength of $\lambda em$ of 615 nm. The sample is in contact with the sensor layer. If glucose penetrates into the sensor layer, hydrogen peroxide can form as a result of enzymatic oxidation and is detected by means of a lanthanoid-ligand complex. A cross-section through an example of a sensor membrane is shown in FIG. 8.

Depending on the substrate to be determined it is possible to use different enzymes. Suitable enzymes are for example the oxidases for lactate, ethanol, bilirubin, cholesterol, various amino acids (e.g glutamate and lysine) and amines (e.g. catecholamines), hydroxyphenols (e.g. tyrosine) and (hypo) xanthine, uric acid and derivatives thereof. In this manner it is possible to provide methods for determining other substrates.

The sensor membranes described above are preferably used for non-invasive determinations. For example it is possible to determine samples of blood, serum, saliva, urine, milk, fruit juices, must, meat, fish or bioreactor liquids.

In addition there is for example a need in the medical field for a method for in vivo determination. The method according to the invention can also be used to carry out in vivo measurements. For this purpose in one embodiment of the method according to the invention a polymer sensor membrane described above (which for example contain glucose oxidase in or on the membrane) is mounted on the tip of a wave guide preferably a fibre optic wave guide. In this manner it is possible to obtain fibre optic sensors like those described in the literature for other systems (Wolfbeis, Fiber Optic Chemical Sensors and Biosensors, CRC Press, Boca Raton, Fla., 1991).

The present invention also encompasses a method in which the changes in the light absorption of the lanthanoid-ligand complex are measured in the wavelength range between 200 and 500 nm, preferably between 300 and 450 nm.

A change in the luminescence of the lanthanoid-ligand complex can be determined by irradiating the lanthanoid-ligand complex with light of wavelengths between 300 and 500 nm, preferably 350 to 450 nm and measuring the change in the decay time of the emission or the change in the intensity of the emission at wavelengths of more than 500 nm, preferably at 550 to 650 nm.

In order to suppress the self-fluorescence of the test material or the system, an excitation impulse is preferably firstly carried out and the luminescence of the lanthanoid-ligand complex is determined after a delay phase of 0.1 to 50 µs, preferably of 2 to 5 µs. A xenon lamp, a blue, violet or ultraviolet light-emitting diode or a blue, violet or ultraviolet laser diode are for example used as a light source in the method according to the invention.

In a preferred embodiment the present invention provides a method in which the formation of hydrogen peroxide is monitored kinetically and the concentration of the analyte is detected or quantitatively determined by means of the change in the optical properties of the lanthanoid-ligand complex that occur per time unit.

A further preferred embodiment provides a method in which the formation of hydrogen peroxide is determined at the end of the reaction and the analytes are detected or determined by the total change in the optical properties of the lanthanoid-ligand complex that occur.

During the determination method according to the invention hydrogen peroxide is formed by the oxidase activity which can be detected by means of a lanthanoid-ligand complex. Surprisingly hydrogen peroxide causes a measurable change in the optical properties of the lanthanoid-ligand reagent and in particular of the absorption and luminescence properties. An advantage of the lanthanoid-ligand complexes according to the invention is their Stokes shift and their decay times which are in the microsecond range. This enables an interfering background fluorescence to be allowed to firstly decay in a time-resolved measurement and the fluorescence of the lanthanoid-ligand complex to be only determined afterwards which results in extremely low detection limits.

A special feature of lanthanoid-ligand complexes is an energy transfer in which the photonic energy taken up by the ligand is transferred to the lanthanoid ion and is released as lanthanoid emission. This luminescence often has a narrow band width (e.g. line shaped), shifted by up to 250 nm into the long wavelength range and has a lifetime in the range of µs up to a few milliseconds. Suitable trivalent ions of the lanthanoid elements can be used as markers in luminescence immunoassays. In one method (DELFIA™) the antibody is labelled with a non-fluorescing lanthanoid ion and, after formation of the immune complex, is admixed with two reagents (chelator and micelle former) which leads to a considerable increase in the intensity of the fluorescence. The method is described in *Fluorescence Spectroscopy: Methods & Applications,* Wolfbeis, O. S., editor: Springer Verlag, Heidelberg, 1993, p. 259–265). A further overview is given in *Anal. Chem.* 62 (1990) 1149A.

In another immunoassay a lanthanoid-ligand complex (e.g. the phenanthroline dicarboxylic acid BCPDA) is added via an avidin-biotin binding reaction and subsequently a solution of Eu(III) nitrate is added. After drying the fluorescence is read preferably with time delays of up to a few 100 µs in order to allow decay of the interfering background fluorescence of the biological material. An overview is given in *Clinical Biochemistry* 21 (1988) 173.

The lanthanoids used as markers in the methods described above must be covalently linked to a protein. The lanthanoid-ligand complexes according to the invention advantageously do not require a covalent binding of the lanthanoid to a protein or to an organic ligand.

The invention also concerns lanthanoid-ligand complexes having the general structure:

$$\text{Ln(III)}_x\text{-Lig}_y$$

in which

Ln(III) is a trivalent ion from the group of lanthanoids, x and y are independently integers from 1 to 20 and the ratio of x:y is 10:1 to 1:3 and Lig is an organic ligand that binds to the lanthanoid ion, wherein hydrogen peroxide causes a change in the absorption or fluorescence properties of the lanthanoid-ligand complex.

Suitable organic ligands have the general structure $R^1$—CO—C($R^2$)=C(X)—$R^3$, in which no more that two of the residues $R^1$, $R^2$ or $R^3$ can be H, X can be OH, $NHR^4$, $NR^4_2$, $R^1$ to $R^4$ can be H, an alkyl, a cycloalkyl, an alkanoyl, a cycloalkanoyl, an aroyl, $CF_3$, a substituted or non-substituted alkyl residue or an alkanoyl residue, OH, $NH_2$, alkylamino or dialkylamino, where each of the residues $R^1$ to $R^4$ can be linked via a substituted or unsubstituted carboxylic or heterocyclic ring to one of the other residues $R^1$ to $R^4$ and $R^1$ to $R^4$ has 1 to 30 and preferably 1 to 12 C atoms.

The organic ligand preferably has 1 to 30 C atoms. Suitable substituents are for example linear or branched alkyl residues having 1 to 30 carbon atoms, in particular 1 to 8 carbon atoms, alkoxy residues with 1 to 30, preferably 1 to 8 carbon atoms, aryl residues, preferably phenyl residues, alkylphenyl or alkoxyphenyl residues or —SR, in which R is a group with 1 to 30 and in particular 1 to 8 carbon atoms. Other suitable substituents are —($CH_2$—$CH_2$—O)$_m$ or —O—($CH_2$—$CH_2$—O)$_m$—$CH_3$ in which m is a number from 1 to 20, in particular 1 to 10.

The lanthanoid of the lanthanoid-ligand complex is preferably europium, terbium, holmium, dysprosium, lanthanum, erbium or samarium and most preferably europium, terbium and holmium.

The organic ligand of the lanthanoid-ligand complex is preferably benzoylacetone, benzoyltrifluoroacetone, dibenzoylmethane, thenoyltrifluoroacetone, a heterocyclic (ortho-hydroxy) carboxylic acid, an aromatic or heterocyclic ortho-hydroxyketone or a derivative thereof, hydroxyquinone, a partially hydrogenated and substituted hydroxyquinone-like compound, an anellated carbocyclic compound such as tetracycline or a tetracycline derivative. The organic ligand is preferably not covalently bound to the lanthanoid.

Lanthanoid-ligand complexes can be present in a solid, dissolved or immobilized form.

A particularly preferred lanthanoid-ligand complex is an europium-tetracycline complex (EuTc) where the stoichiometic ratio of europium to tetracycline does not have to be 1:1. Hydrogen peroxide has a particularly strong effect on EuTc. The effect of hydrogen peroxide on EuTc is shown for example in FIG. 1. The EuTc shows the typical spectral properties of a europium ligand complex. Its absorption maximum is at 395 to 405 nm, its absorbance (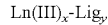) increases considerably in the presence of hydrogen peroxide, this can be used to determine oxidase-catalysed reactions.

The emission of EuTc exhibits characteristic lines at 615 nm in the visible spectral range. The luminescence is preferably excited with light of wavelengths between 300 and 450 nm, preferably by means of a light emitting diode. The luminescence is amplified by hydrogen peroxide. The fluorescence of other lanthanoid-ligand complexes in which the lanthanoid ion is for example dysprosium, holmium or samarium are also influenced by hydrogen peroxide and this is for example shown in FIGS. 2 to 4.

The present invention is elucidated by the attached figures and the following examples.

Figure 1:
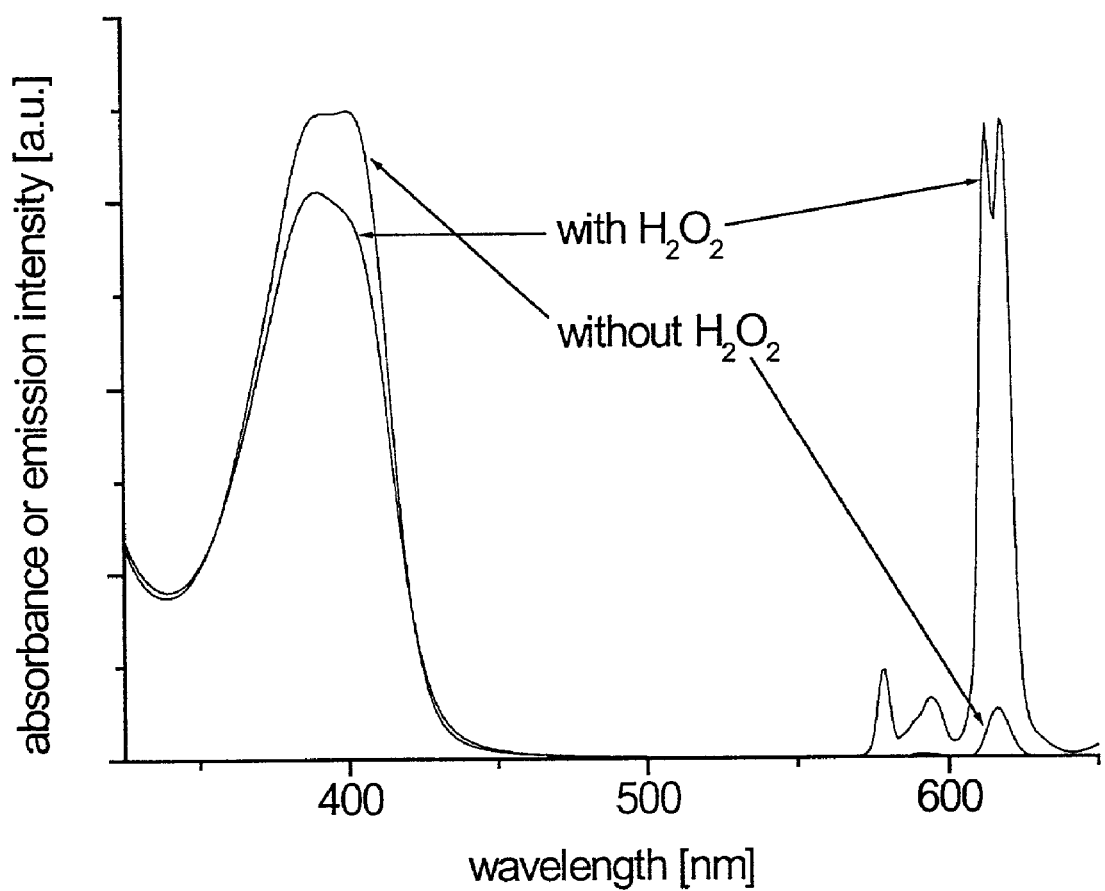
FIG. 1 shows the absorption and emission spectra of the EuTc complex in the absence and in the presence of $H_2O_2$. Although the absorption at 400 nm decreases slightly when $H_2O_2$ is added, the emission intensity at ca. 615 nm increases by up to 15-fold.
Figure 2:
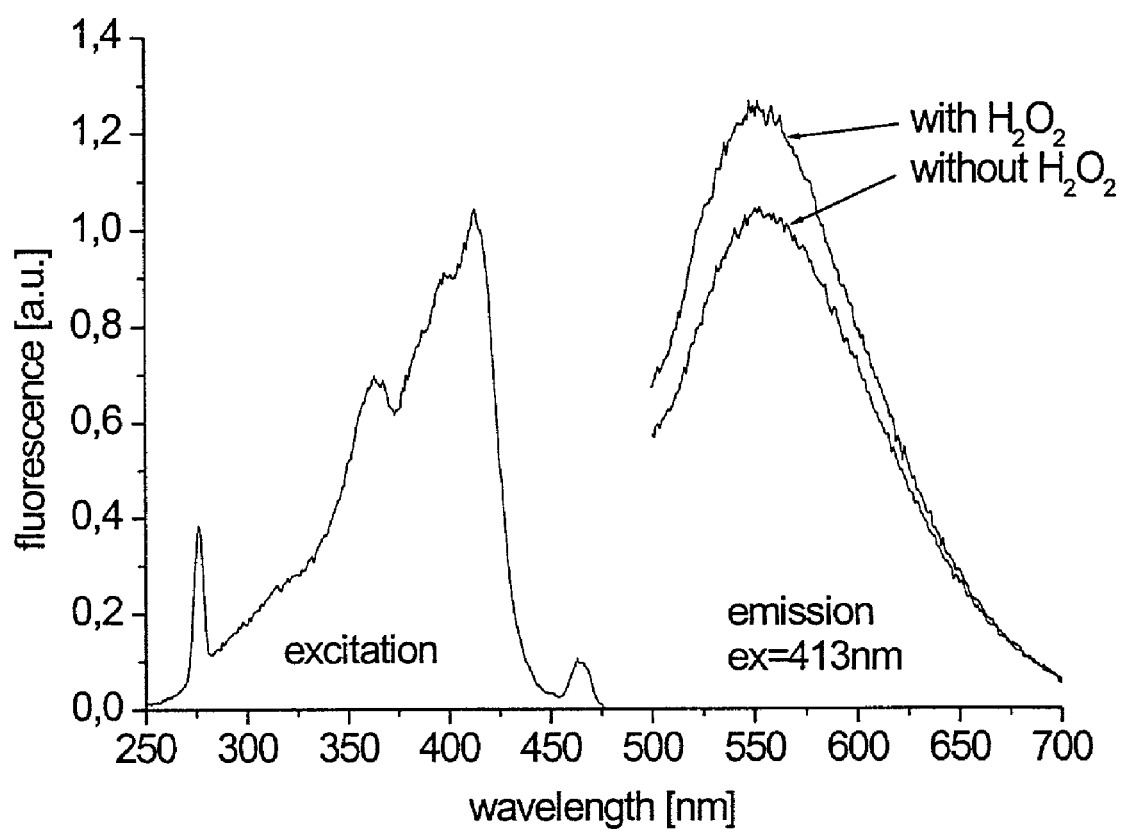
FIG. 2 shows the influence of hydrogen peroxide on the emission spectrum of the dysprosium(III) tetracycline complex in water at pH 6.9.
Figure 3:
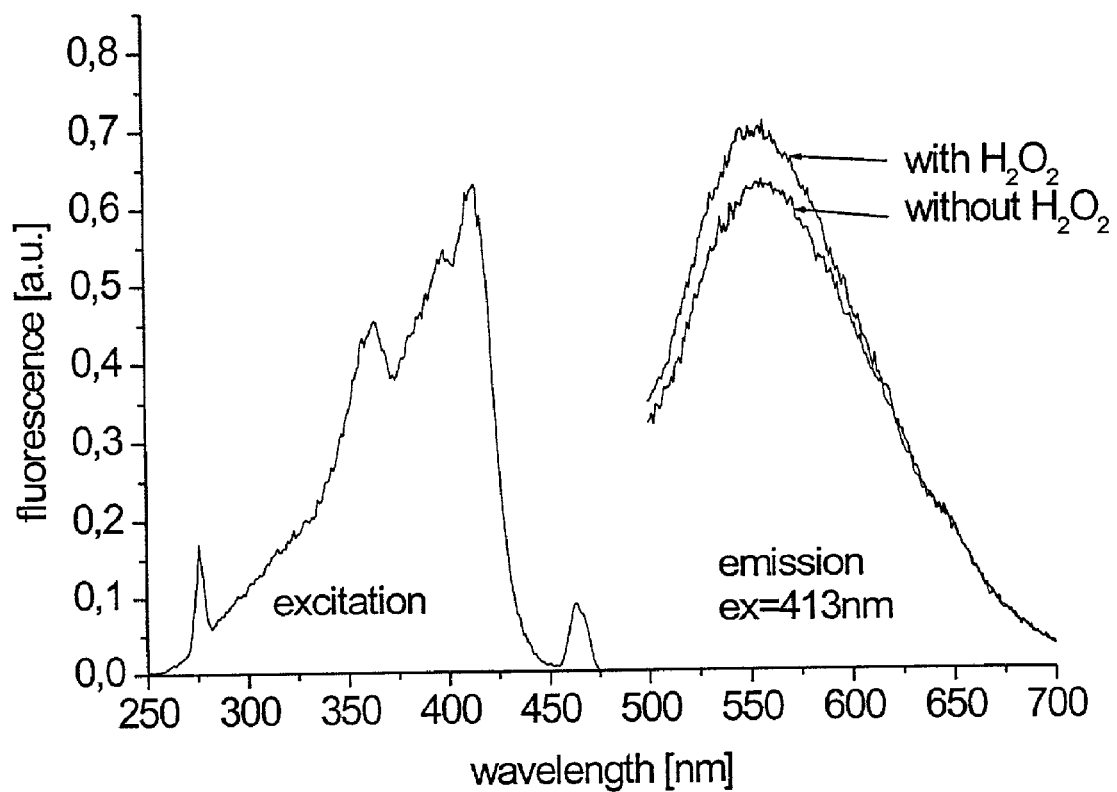
FIG. 3 shows the influence of hydrogen peroxide on the emission spectrum of the holmium(III) tetracycline complex in water at pH 6.9.
Figure 4:
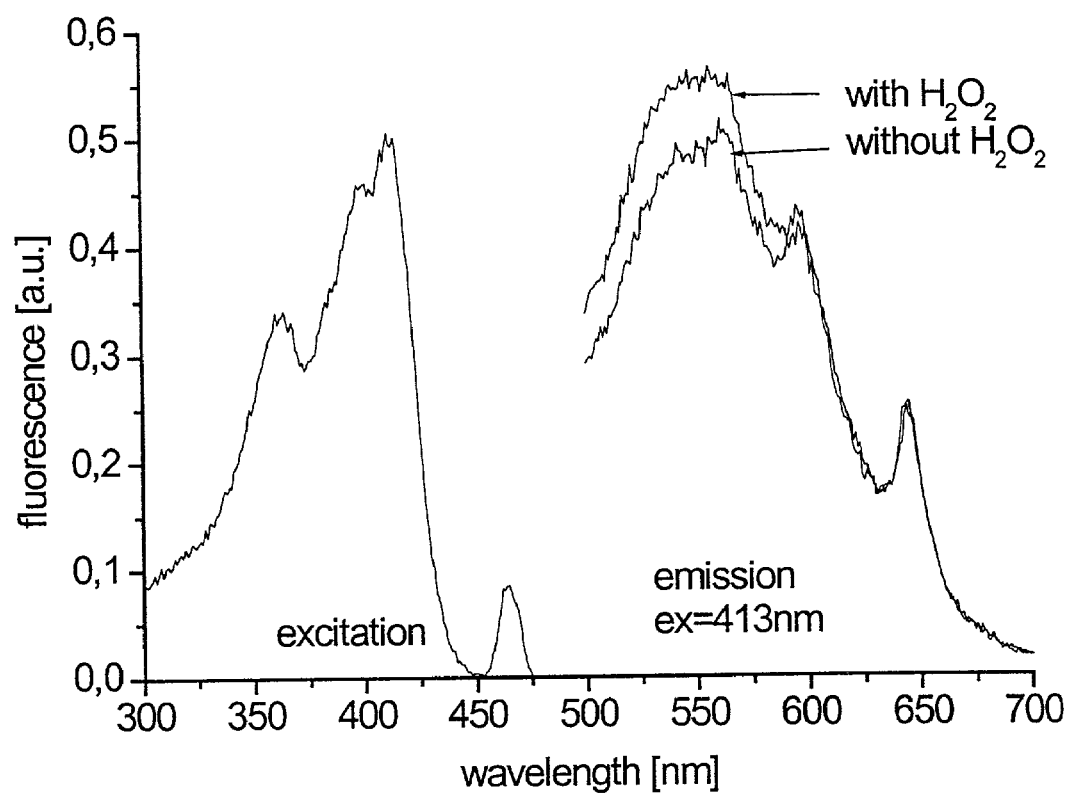
FIG. 4 shows the influence of hydrogen peroxide on the emission spectrum of the samarium(III) tetracycline complex in water at pH 6.9.
Figure 5:
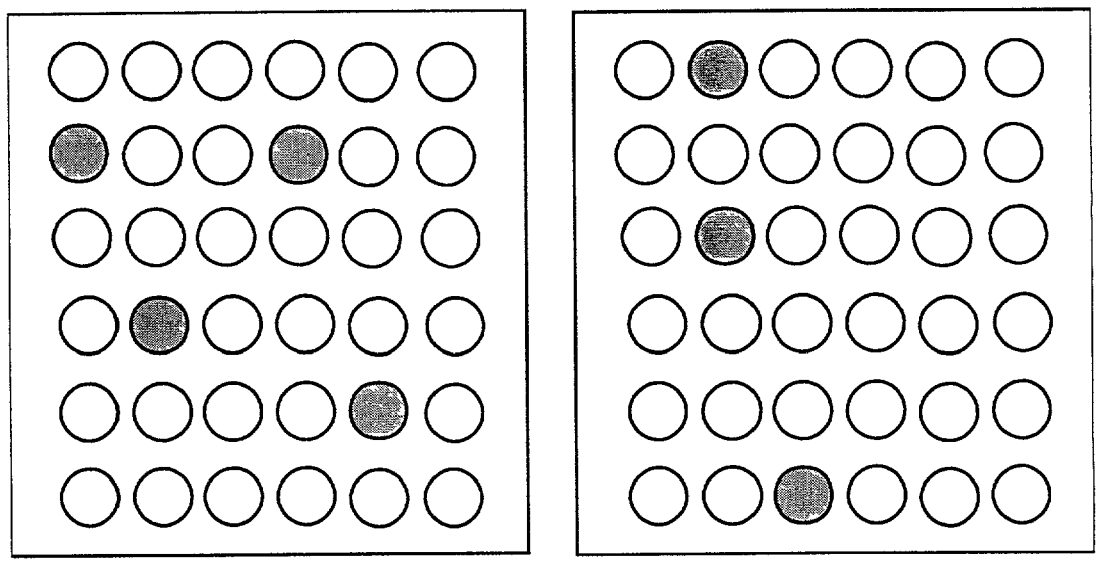

FIG. 5 shows a part of a microtitre plate in the wells of which various enzymes, (lipases, dehydrogenases, glucose oxidase) have been introduced. Subsequently the corresponding enzyme substrate (glucose) and a reagent according to the invention (EuTc) were added. Left part: dark spots represent bright fluorescence. This occurs at positions where glucose oxidase is located. Positions where dehydrogenases or lipases were located, remained clear (no fluorescence). In this manner patterns are obtained which are typical for each enzyme pattern (e.g. from bacteria). Right part: Human serum albumin was labelled with various enzymes (for example glucose oxidase) and placed in the wells. After adding EuTc and glucose, a strong fluorescence is only found at those positions where glucose oxidase-labelled HSA is located. In contrast wells in which HSA was labelled with non-oxidases (e.g. glucose dehydrogenase) were clear.

Figure 6:
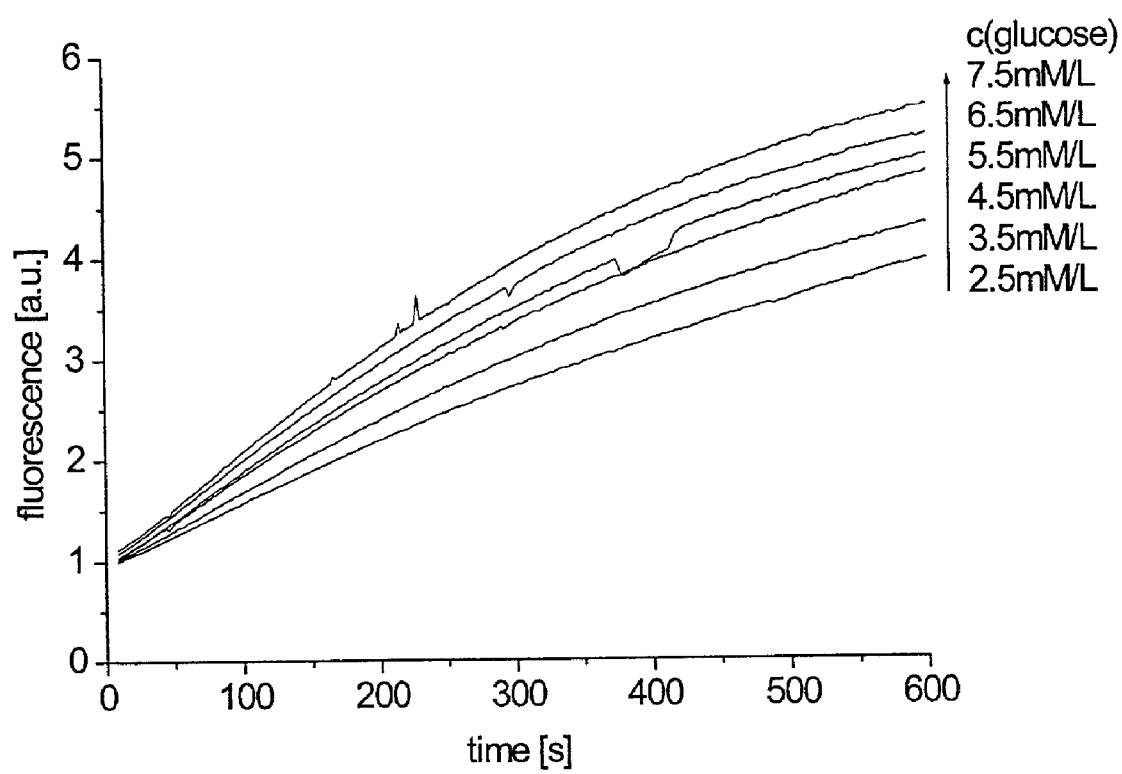

FIG. 6 shows the increase with time of the luminescence intensity of the reagent EuTc in the presence of glucose oxidase and a serum which contains glucose in various physiological concentrations. The change in the luminescence intensity per 3 min served as the analytical information.

Figure 7:
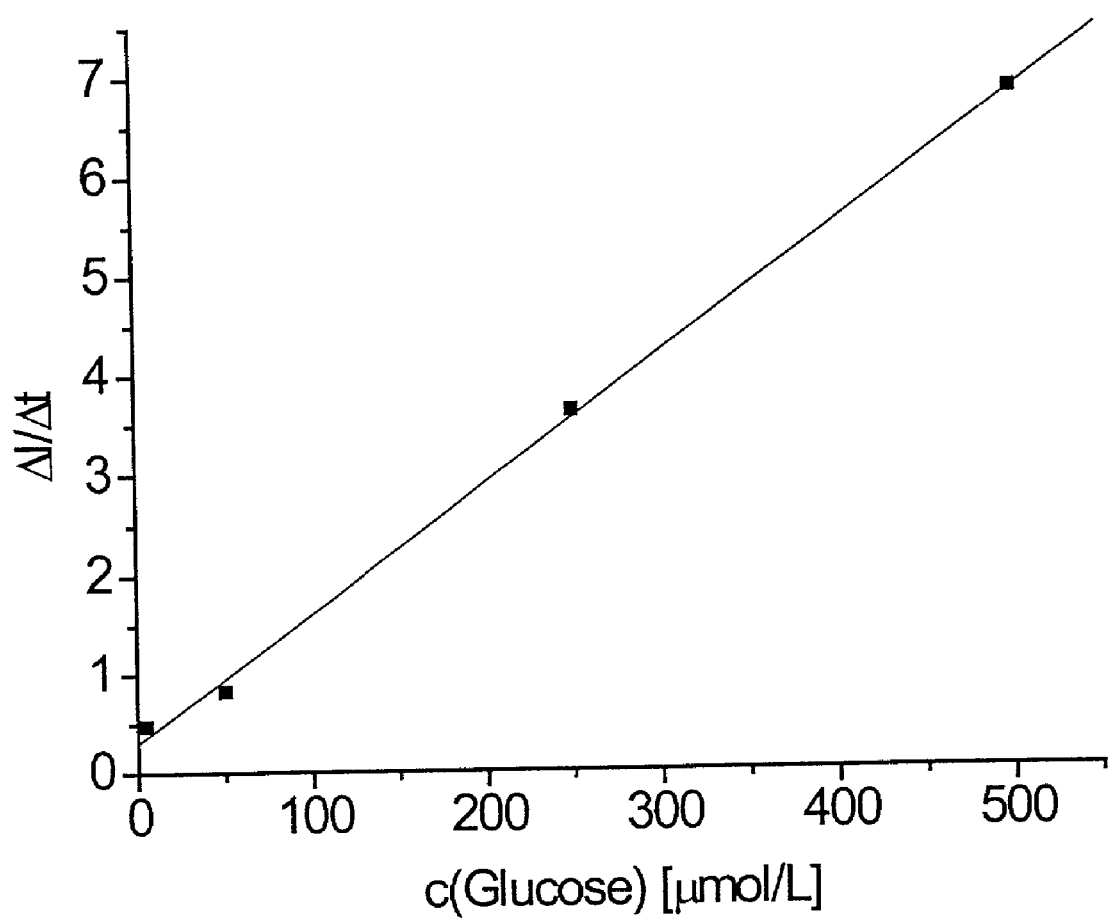

FIG. 7 shows a calibration curve for the determination of glucose with the aid of glucose oxidase and the reagent EuTc in water at pH 6.9 by plotting the change in the fluorescence intensity per time [$\Delta F/\Delta t$] against the glucose concentration.

Figure 8:
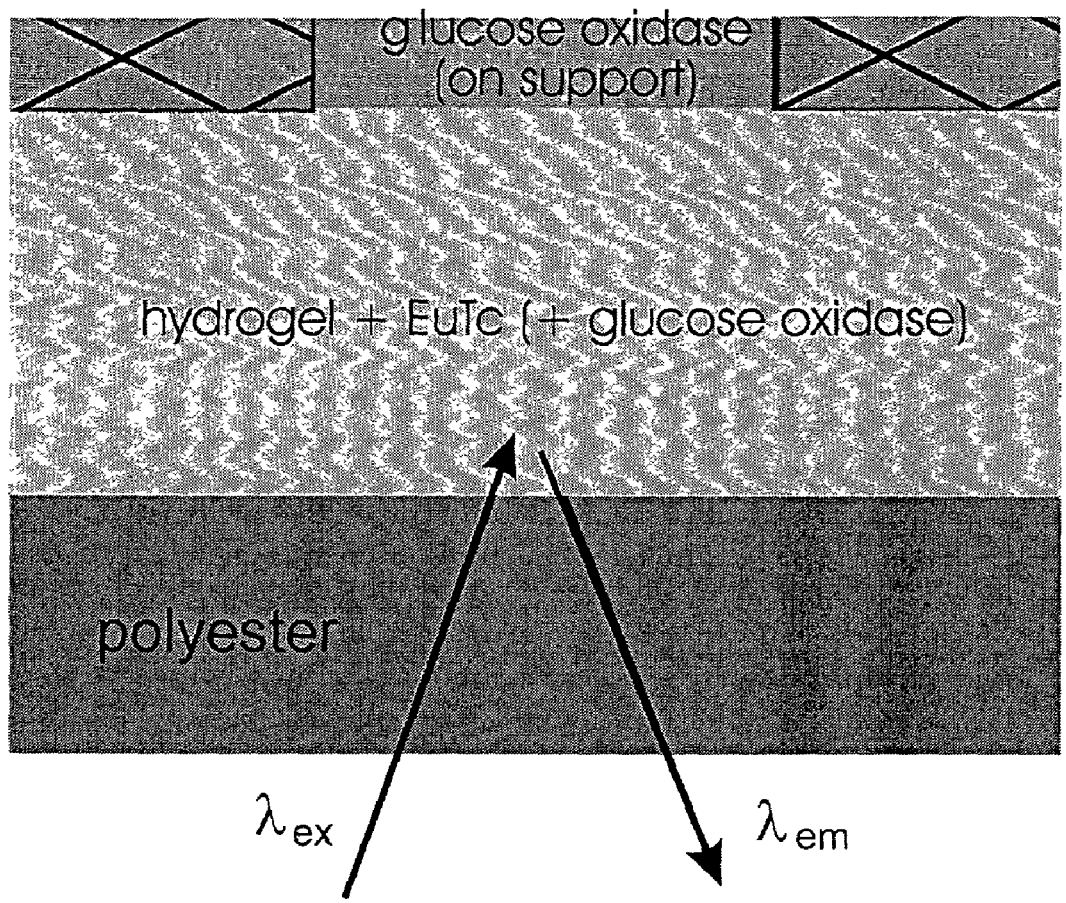

FIG. 8 shows a cross-section through a sensor membrane for glucose. A lower layer consisting of a hydrogel polymer containing an indicator according to the invention (in the present case EuTc) lies on an inert but optically transparent polyester layer. The overlying layer consists of glucose oxidase that had been immobilized on a support made of nylon net. The fluorescence of the EuTc is scanned from the polyester side by irradiating it at an excitation wavelength $\lambda_{ec}$ of 405 nm and measuring the emission at a wavelength of $\lambda_{em}$ of ca. 615 nm. The sample is in contact with the sensor layer. When glucose penetrates into the sensor layer, hydrogen peroxide is formed by enzymatic oxidation and this is indicated by an increase in the fluorescence intensity (and in a decrease in the decay time) of the reagent.

Figure 9:
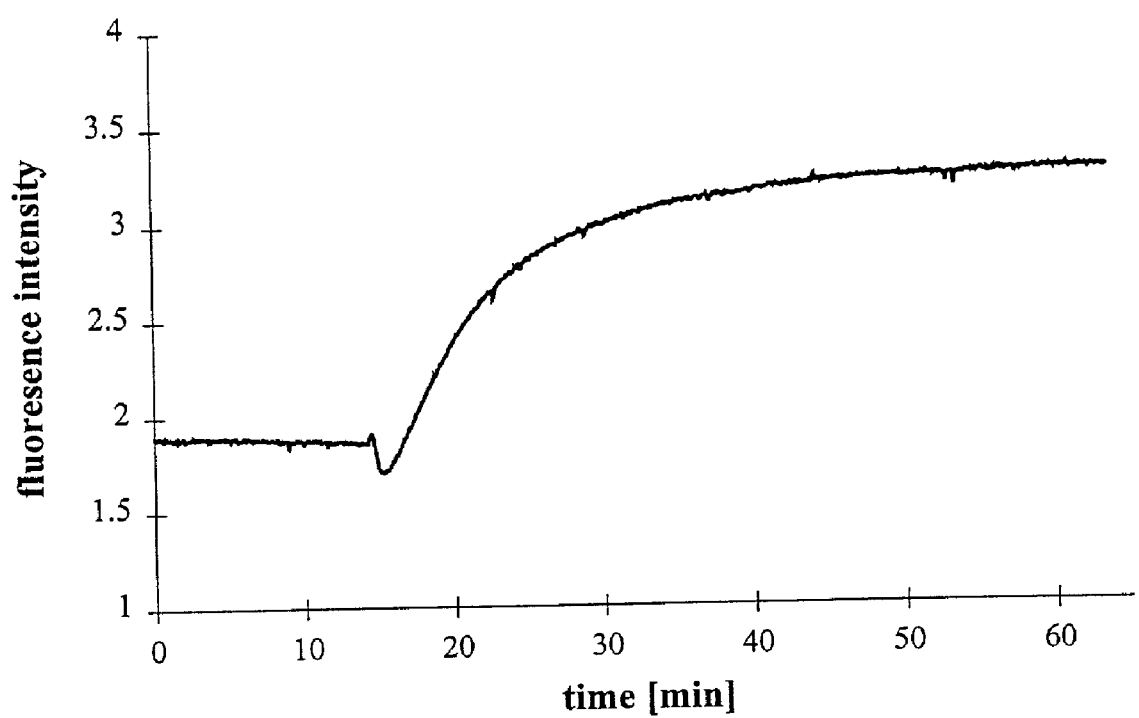

FIG. 9 shows a time course of the response of a polymer sensor membrane (as shown in FIG. 8) containing an indicator (EuTc) to a 1% solution of glucose in a buffer at pH 6.9. The sensor membrane was mounted in a flow cell which was located in a fluorometer. The glucose solution was pumped through the cell across the sensor membrane and the change in the fluorescence intensity was plotted against time. The initial decrease is due to the ingress of an air bubble.

Figure 10:
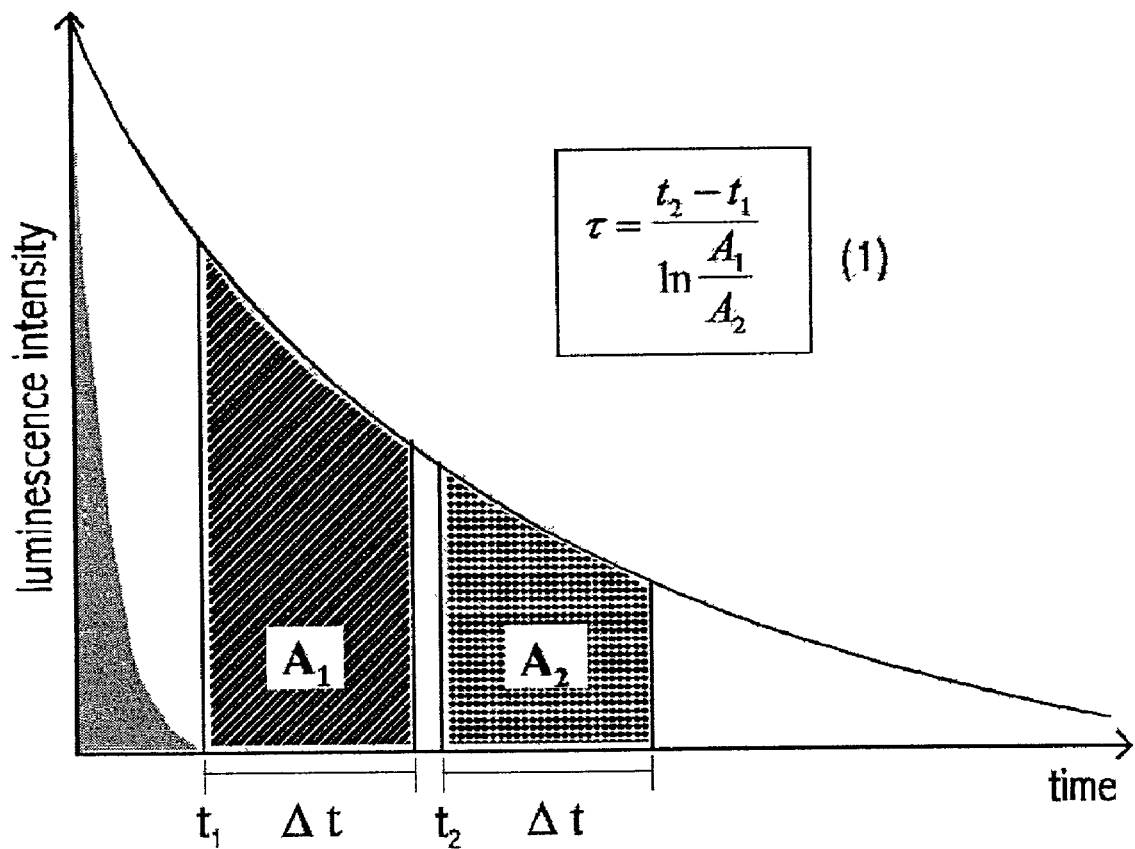

FIG. 10 shows a schematic representation of a time-resolved measurement for suppressing the background fluorescence caused by biological materials. It is excited with a short light pulse, then one waits until time point $t_1$ until the background fluorescence has almost completely decayed (typically after 100–500 ns) and then the measuring window is opened. It is now possible to either determine an integral fluorescence intensity $A_1$ or determine the decay time of the system by determining $A_1$ and $A_2$ (and using the stated equation) that can also serve as an analytical quantity to be measured. Both methods are used to suppress the interfering background fluorescence.

EXAMPLE 1

Preparation of a Lanthanoid-ligand Complex (EuTc)

In order to prepare the buffer, 1.48 g MOPS Na$^+$ salt (Fluka AG) is dissolved in 490 ml distilled water, the pH of the solution is adjusted to pH 6.9 with a small amount of 70% perchloric acid and it is filled up to a final volume of 500 ml. The reagent solution is obtained by dissolving 4.0 mg tetracycline hydrochloride (Fluka AG) and 9.6 mg EuCl$_3$ hexahydrate (Alfa) in 100 ml of the above buffer. The reagent can be obtained in a dry form by preparing the dissolved reagent without the buffer addition and then freeze-drying the solution. Other quantity ratios of tetracycline to europium ion are possible.

EXAMPLE 2

Enzymatic Determination of Glucose in Serum

Glucose oxidase stock solution: 2.0 mg glucose oxidase (50,000 units, Sigma) is dissolved in 10 ml MOPS buffer.

Method of determination: 1 ml of the reagent, 1 ml of the serum to be determined for glucose (containing 3–50 mmol/l glucose) and subsequently 1 ml of the glucose oxidase stock solution were filled into a fluorescence cuvette. The increase of the fluorescence intensity is monitored over time starting at the time of glucose oxidase addition. The increase in fluorescence after a defined time e.g. after 3 min is a measure for the concentration of glucose present in the serum. The exact value can be calculated with the aid of calibration curves previously determined with the aid of standard solutions (as shown in FIG. 7).

EXAMPLE 3

Determination of Xanthine

Principle: Xanthine (+xanthine oxidase)=>uric acid+ $H_2O_2$

The amount of hydrogen peroxide formed depends on the concentration of xanthine and can be detected with the aid of a reagent according to the invention.

Method of determination: 1 ml of the reagent solution described in example 1 and 1 ml of a solution of 4.5 enzyme units xanthine oxidase (Sigma; E.C. No. 1.1.3.22) in 10 ml of a 0.015 molar phosphate buffer are pipetted into a 5 ml cuvette. Afterwards 1 ml of the solution to be analysed for xanthine (which should contain between 0.5 and 5 mM xanthine) is added and the increase in the fluorescence is measured immediately afterwards between 600 and 640 nm with a light excitation at 400–410 nm. The increase in fluorescence over time is a measure of the xanthine concentration. The data for setting up a calibration curve are obtained by using diluted solutions of xanthine in the same buffer (having a xanthine content between 0.1 and 10 mM) instead of the solution to be analysed. A calibration curve is obtained by plotting the change in fluorescence ($\Delta F$) per time (2–5 min) against the concentration of xanthine.

EXAMPLE 4

Determination of Glucose in Serum with the Aid of an Automated Flow System Using Immobilized Glucose Oxidase and a Hydrogen Peroxide Sensor Principle: glucose (+glucose oxidase)=====>gluconolactone+$H_2O_2$ Method of determination: A flow injection system from the Eppendorf Co. (Hamburg) was used. A HEPES buffer at pH 6.9 is used as the flow solution. The samples were prepared by diluting the human sera to be examined 1:1 with HEPES buffer (pH 6.9). The glucose oxidase was immobilized on agarose as follows: glucose oxidase was reacted with the reagent biotin-amidocaproate-NHS ester (Sigma, prod. No. B 2643) according to the instructions. The glucose oxidase biotinylated in this manner (also commercially available, Sigma G 7779) was immobilized on agarose beads which carry avidin groups on their surface (Sigma; product No. A 9207). The binding between avidin and biotin is very strong. A small plastic tube was filled with the resulting beads, both ends were closed with cotton-wool, the reaction chamber obtained in this manner was then attached to the flow system and filled with buffer.

The hydrogen peroxide sensor is prepared by preparing a 5% solution of the hydrogel HN80 (from Kingston Technology Inc., Dayton, N.J., USA) in dimethyl-sulfoxide (DMSO). A 100 μm thick coat of this viscous liquid was applied to a polyester foil and subsequently allowed to stand for 4 h in moist air. The resulting clear membrane was washed with water and was about 6–8 μm thick. The membrane was then placed in 100 ml of a solution which contained 0.1% europium chloride and 0.1% tetracycline. After 24 h it was removed, rinsed and was then ready to use. The film obtained was attached to the wall of a small flow cell and this was then connected to the flow system.

The actual determination of glucose was carried out by injecting 100 μl of the serum samples diluted with buffer into the flow system. The injected samples passed through the reaction chamber (containing the immobilized glucose oxidase) and directly afterwards the flow cell containing the hydrogen peroxide sensor.

The system was calibrated with a 5 mM solution of glucose in a HEPES buffer containing 2% albumin. Afterwards 9 samples were analysed and, after each sample, buffer was again pumped through the analyzer until the fluorescence signal of the sensor had again returned to the initial value. After examining 9 samples a calibration with a 5 mM glucose standard was again carried out.

The fluorescence emitted by the sensor membrane in the flow chamber served as the analytical signal. It was excited at 410 nm, the fluorescence intensity was measured at >600 nm and integrated over a time of 60 sec which corresponds to the residence time of the sample in the flow chamber.

EXAMPLE 5

Determination of Lactate in Serum in a Microtitre Plate

This determination was carried out by adding the enzyme lactate oxidase (Sigma L-0638; concentration 5 mg/200 μl) to 100 μl of a serum sample diluted with buffer pH 6.9 in a microtitre plate and detecting the generated hydrogen peroxide by means of the fluorescence of an added reagent solution (50 μl) which is described in example 1.

EXAMPLE 6

Multi Enzyme Assay for Creatinine

Creatinine in serum is considerably increased in the case of renal malfunction.

Principle: creatinine (+creatininase)===>creatine
creatine (+creatinase)===>sarcosine+urea
sarcosine (+sarcosine oxidase)===>glycine+formaldehyde+$H_2O_2$ The hydrogen peroxide that is formed is detected with the aid of a lanthanoid-ligand reagent according to the invention. Creatine that is also present can be determined in a second preparation in which the first of the 3 reactions is not carried out.

Sample preparation: The serum sample is diluted with a buffer of pH 7.3 in a ratio of 1:1

Method of Determination (a) creatinine+creatine: 200 μl of a sample (with a content of 5–10 mM creatinine) is added first. Then 0.5 ml of the hydrogen peroxide reagent and subsequently a separately prepared solution of 1 mg creatininase (from *Pseudomonas*; free of creatinase; having a total activity of 150–200 units), 10 mg creatinase (from *Flavobacterium*; total activity 100–200 units) and 10 mg sarcosine oxidase (from *Arthrobacter*, total activity 50–150 units) in 0.5 ml phosphate buffer containing 2% HSA is added. The luminescence of the reagent is monitored starting at the time when the enzyme solution is added. The change in luminescence over time (3 min) is a measure of the creatinine concentration.

(b) Only creatine: In order to determine creatine which may be present, the same reaction is carried out but no creatininase is added. In this manner only creatine is measured.

(c) Only creatinine: The value is derived from the difference between the two previous determinations.

EXAMPLE 7

Determination of Total Cholesterol (Multi Enzyme Assay)

Principle: cholesterol ester (+cholesterol esterase)===>cholesterol+fatty acids
cholesterol (+cholesterol oxidase)===>cholest-4-ene-3-one+$H_2O_2$ The amount of hydrogen peroxide that is formed is proportional to the concentration of total cholesterol present in the serum and is determined with the aid of a reagent according to the invention.

EXAMPLE 8

Lactate Determination (Multi Enzyme Assay)

Principle: lactate+NAD (+lactate dehydrogenase===>pyruvate+NADH
pyruvate+phosphate (+pyruvate oxidase)===>acetyl phosphate+$H_2O_2$ The hydrogen peroxide that is formed is determined with the aid of a reagent according to the invention.

EXAMPLE 9

Determination of Triglycerides (Multi Enzyme Assay)

Triglycerides are for example determined in order to diagnose hyperlipoproteinaemias. Hyperlipoproteinaemias are regarded as a risk factor for cardiovascular diseases.

Principle: triglycerides are firstly saponified with lipase and the liberated glycerol is then determined kinetically in a 2-enzyme reaction.

triglycerides (+lipase)===>glycerol+fatty acids
glycerol+ATP (+glycerol kinase)===>glycerol-1-phosphate+ATP
glycerol-1-phosphate (+oxidase)===>dihydroxyacetone phosphate+$H_2O_2$ The hydrogen peroxide formed is determined with the aid of a reagent according to the invention.

EXAMPLE 10

Determination of the Activity of the Enzyme Alanine Aminotransferase (ALT)

This enzyme has a diagnostic significance since its activity is increased in various liver diseases (in particular hepatitis). It is determined in a multi enzyme method by the following reaction sequence:

L-alanine+2-ketoglutarate (+ALT)===>pyruvate+ glutamate
pyruvate+phosphate (+pyruvate oxidase) ===>acetylphosphate+$H_2O_2$ The amount of hydrogen peroxide formed is proportional to the activity of the enzyme ALT and is determined with the aid of the reagent according to the invention.

EXAMPLE 11

Determination of the Activity of Alkaline Phosphatase (ALP)

The activity of this enzyme is greatly increased in diverse diseases (for example tumours) of the liver and bones.
Principle: tyrosine-phosphate (+ALP)===>tyrosine
tyrosine (+tyrosine decarboxylase)===>tyramine
tyramine (+tyramine oxidase)===>p-hydroxyphenylacetaldehyde+$H_2O_2$ The amount of hydrogen peroxide formed is proportional to the activity of the enzyme ALP and is determined with the aid of a reagent according to the invention.

EXAMPLE 12

Determination of the Activity of Choline Esterase

The activity of this enzyme is considerably decreased in the case of neurotoxin poisoning.
Principle: acetylcholine (+choline esterase)===>acetate+ choline
choline (+choline oxidase)===>betaine+$H_2O_2$ The hydrogen peroxide formed is determined with the aid of the reagent according to the invention.

EXAMPLE 13

Determination of the Activity of Lactate Dehydrogenase

The activity of this enzyme is greatly increased after a myocardial infarction.
Principle of a Self-amplifying Reaction Sequence:
pyruvate+NADH (+lactate dehydrogenase)===>lactate
lactate (+lactate oxidase)===>pyruvate+$H_2O_2$ The amount of hydrogen peroxide formed depends on the activity of lactate dehydrogenase and can be determined with the aid of a reagent according to the invention.

EXAMPLE 14

Determination of Inhibitors of HIV Proteinase

Inhibitors of this enzyme are potential HIV drugs.
Principle: Proteases can cleave a terminal amino acid (AA) from peptides. Inhibitors considerably slow down the activity of the protease which results in a decreased formation of hydrogen peroxide.

Peptide (+HIV proteinase)===>amino acid (e.g. Ala; Leu)+residual peptide
amino acid (+AA oxidase)===>
===>oxidized amino acid (e.g. pyruvate, α ketoisocaproate)+$H_2O_2$ The amount of hydrogen peroxide formed depends on the activity of the HIV proteinase and can be determined using a reagent according to the invention. The first reaction is considerably inhibited by inhibitors of HIV protease e.g. by acetyl pepstatin (Richards et al., *FEBS Letters* 253 (1989) 214).

EXAMPLE 15

Determination of an Antigen (HSA) by an Immunoassay Based on Magnetic Particles (a) Biotinylation of anti-HSA: polyclonal anti-HSA (goat; Sigma Prod. No. A-1151) was diluted 10-fold with phosphate buffer and reacted with the biotinylation reagent biotin-amidocaproic acid sulfo-NHS ester (Sigma, B-1022) according to the instructions of Psantano et al., (*Analytical Chemistry* 65 (1993) 623). The anti-HAS biotinylated in this manner was then bound to magnetic particles (see example 15 (c)).

(b) Labelling of anti-HSA with glucose oxidase: It was labelled by means of the biotin-streptavidin binding reaction. Polyclonal anti-HSA (goat; Sigma prod. No. A-1151) was diluted 10-fold with phosphate buffer and firstly labelled with streptavidin-maleinimide (Sigma, prod. No. S-9415) according to the instructions of Duncan et al. in *Analytical Biochemistry* 132 (1983) 68. After electrophoretic purification the streptavidin/anti-HSA conjugate formed in this way was mixed with the glucose oxidase labelling reagent biotinamino glucose oxidase (Sigma No. G-7779) and electrophoretically purified.

(c) Immobilization of anti-HSA on magnetic beads: The immobilization was carried out with the aid of a biotin-streptavidin binding reaction. 1 ml of a suspension of paramagnetic iron oxide particles with surface-bound streptavidin (d=1 μm, Sigma; prod. No. S-2415; containing about 1 mg immobilized streptavidin) was admixed with 1 ml of a solution of biotinylated anti-HSA (see under (a)) and allowed to stand for 1 h at room temperature. The particles were then separated with the aid of a magnetic separator (Sigma, prod. No. M-1292).

(d) Method of determination: The magnetic particles obtained according to (c) were suspended in 2 ml phosphate buffer pH 7.0 and admixed with solutions containing between 2 and 20 μg/ml HSA which corresponds to the concentration of HSA in urine or in the case of microalbuminuria. After 10 min the particles were separated by a magnetic separator, resuspended in 2 ml PBS and admixed with a solution of 1 mg/ml of the glucose oxidase-labelled polyclonal anti-HSA (see b). In such a sandwich assay the anti-HSA binds to the HSA that is already on the particles. After another magnetic separation and resuspension, a 0.1% solution of glucose in PBS and 1 ml of a solution containing 0.1% tetracycline (Sigma, prod. No. T-3258) and 0.1% europium chloride (Fluka) were added. The amount of hydrogen peroxide formed per unit of time can be determined by the increase in fluorescence at 610–620 nm (with excitation at 405 nm) and is proportional to the concentration of HSA in the sample.

EXAMPLE 16

Detection of a Specific Oligomer Sequence by Means of a Hybridization Assay

Principle: Binding of a glucose oxidase-labelled 16mer to a complementary 16mer that had been immobilized on an agarose particle was detected by means of the glucose oxidase activity that was detectable by reagents according to the invention.

(a) Preparation of a streptavidin-labelled galactose oxidase Galactose oxidase (E.C.1.1.3.9) was labelled in a known manner with a streptavidin maleinimide reagent (Sigma, S-9415) and purified.

(b) Preparation of an oligomer labelled with galactose oxidase: The immobilization was achieved by conjugating a biotinylated 16mer having the sequence [biotin-$(CH_2)_6$-ATTACCGGACTCTATA-3'] (Metabion GmbH, Munich) to a streptavidin/glucose oxidase conjugate described in example 15 and subsequently electrophoretic purification.

(c) Preparation of a particle-bound oligomer: The aminomodified sequence [3'-TAATGGCCTGAGATAT-$(CH_2)_6$-$NH_2$] was covalently conjugated with the aid of the coupling reagent EDAC (Sigma, E-1769) to the carboxy group of carboxymodified latex particles (Bangs Labs. Inc.; d=20 μm) suspended in TRIS buffer (pH 7.5). The particles were centrifuged, washed and resuspended in TRIS buffer.

(d) Hybridization and detection of the activity of glucose oxidase: The particle suspension (1 ml) described in example 15 was admixed with 100 μl of a solution of glucose oxidase-labelled oligomer and hybridized at 55° C. The particles were centrifuged after 1 h, washed and resuspended in buffer. After adding 500 μl of a 0.1% solution of galactose and 500 μl of a solution containing 0.1% europium nitrate and 0.1% tetracycline, a considerable increase in the fluorescence at 610–620 nm (with excitation at 405 nm) was found.

This is proof of a hybridization of the glucose oxidase-labelled strand. When other glucose oxidase-labelled sequences were used no formation of hydrogen peroxide occurred due to the absence of hybridization (and thus to the absence of glucose oxidase in the particles).

EXAMPLE 17

Example of a Time-resolved Measuring Procedure

The fluorescence of the lanthanoid reagents according to the invention decays relatively slowly (as shown in FIG. 10). In the measurement procedure the lanthanoid complex is excited with a short (0.01–0.1 μs) pulse of a UV light-emitting diode (Nichia; $\lambda_{max}$ at 375 nm). The emitted light intensity is then integrated after a delay time $t_1$ which depends on the decay time of the lanthanoid complex and should preferably not exceed 10 μs. One can also determine decay times by determining the ratio of two areas ($A_1$ and $A_2$) (*Appl. Spectrosc.* 54 (2000) 548–559). The corresponding scan scheme is shown in FIG. 10.

The analytical information from the method according to the invention is not only the measurement of the change in the luminescence intensity but also the measurement of the change in the luminescence decay time. In the absence of hydrogen peroxide EuTc has a main decay time of 12.4 μs but the decay time after saturation with hydrogen peroxide is 9.0 μs. In this measurement method one preferably excites the fluorescence with a violet light-emitting diode or a UV LED (Nichia) and determines the decay function of the emitted light which is freed of violet and blue light components on the emission side with the aid of an OG 570 long pass filter.

EXAMPLE 18

Preparation of a Biosensor Membrane Containing Immobilized Enzyme and Immobilized Lanthanoid-ligand Indicator 2 g of a hydrogel (Hypan; from Hymedix, Dayton, Ohio) is dissolved in 20 g dimethylsulfoxide (Merck) and the solution is coated on a 120 μm thick transparent polyester foil (Mylar™; from Goodfellow). After evaporating the solvent over water, the remaining layer has a thickness of ca. 12 μm. Spots (Ø 3–10 mm) were punched out of the coated foil and placed for 5 h in an EuTc reagent solution (see example 1). The layer is coloured yellow. The yellow spots were allowed to stand for 24 h in a 5 mM MOPS buffer (without EuTc) and were then ready to use. This sensor membrane is then covered with a 2 μm thick layer consisting of 9 parts by weight p-HEMA (poly-hydroxyethyl methacrylate, Sigma P 3183) or polyacrylamide and one part by weight of the glucose oxidase PAA conjugate (Sigma, product No. G-9255). The response of such a sensor membrane to a solution of glucose is shown in FIG. 8.

EXAMPLE 19

Method for Determining an Enzyme Inhibitor (Heavy Metal Ion) Using a Biosensor Membrane at the Bottom of the Well of a Microtitre Plate (a) Pretreatment of the microtitre plate (MTP): Sensor spots were glued to the bottom of a standard MTP with 96 wells which were obtained by punching out a biosensor area as described in example 18 except that the nylon surface was not coated with glucose oxidase but with glutamate oxidase (E.C.1.4.3.11; Sigma No. G-0400).

(b) Reaction sequence:
urea (+urease)=>ammonia+bicarbonate
ammonia+2-oxoglutarate+NADPH (+glutamate-dehydrogenase)=>
=>glutamate+NADP
glutamate (+glutamate oxidase)=degradation product+$H_2O_2$ (c) Determination: The wells of the MTP containing the sensor spots are successively filled, preferably using a automated pipettor with the following solutions:
100 μl of a 10% solution of urea in Tris buffer pH 8.0;
2 mg glutamate dehydrogenase (E.C.1.4.1.3) dissolved in 10 μl Tris buffer:
1 mg NADPH (Na salt; Sigma N-1630) dissolved in 10 μl buffer;

(d) 100 μl environmental sample having a heavy metal content (Ag, Pb, Cu, Cd) in the range of 0.1–10 mg/l;

(e) 10 mg of a solution of urease (E.C.3.5.1.5; Sigma prod. No. U-1500) in 10 μl buffer.

Immediately after addition of urease the retardation of the hydrogen peroxide formation as a result of the inhibition of the heavy metals is measured. The maximum binding rate for hydrogen peroxide is determined by measuring a solution in which 0.5 ml of the environmental sample is replaced by distilled water.

The amount of hydrogen peroxide formed depends on the content of heavy metal ions in the sample solution since the activity of urease is already inhibited by traces of heavy metals (Preininger et al., *Biosensors & Bioelectronics* 11 (1996) 981–990). The time course of the increase in the concentration of hydrogen peroxide is determined by the luminescence of the sensor spots in the wells with the aid of a microtitre plate reader (Ascent Fluoroskan) which scans from below.

The invention claimed is:

1. Method for determining enzymatically generated hydrogen peroxide, comprising determining with the aid of a lanthanoid-ligand complex, hydrogen peroxide that is formed by an enzyme that is a hydrogen peroxide-generating oxidase, wherein the hydrogen peroxide formed by oxidase activity results in a measurable change in light absorption in a wavelength range between 200 nm and 500 nm or in fluorescent properties of the lanthanoid-ligand complex.

2. Method as claimed in claim 1, wherein an enzyme cascade comprising two or several enzymes of which at least one is from the group of oxidases is present.

3. Method as claimed in claim 1, wherein at least one of the enzymes from the group of oxidases is present as a free enzyme, as an oxidase-labelled antibody or as an oxidase-labelled oligomer.

4. Method as claimed in claim 1, further comprising in vivo or in vitro qualitative or quantitative determination of an enzymes, enzyme activity, enzyme substrate, enzyme inhibitor, enzyme activator, antigen or nucleic acid oligomer by determining the measurable change in light absorption in a wavelength range between 200 and 500 nm or in fluorescent properties of the lanthanoid-ligand complex caused by hydrogen peroxide that is formed by the enzyme that is a hydrogen peroxide-generating oxidase, wherein the measurable change in light absorption or in fluorescent properties of the lanthanoid-ligand complex has a known or previously determined relationship to the concentration of the enzyme, enzyme substrate, enzyme inhibitor, enzyme activator, antigen or nucleic acid oligomers.

5. Method as claimed in claim 4, wherein the enzyme substrate is selected from the group consisting of glucose, alcohol, lactate, bilirubin, cholesterol, and creatinine, or wherein the enzyme inhibitor is a toxic substance, or wherein the enzyme activator is a monovalent or divalent metal ion.

6. Method as claimed in claim 1, wherein the enzymatically generated hydrogen is determined in a sample of blood, sperm, saliva, interstitial fluid or other body fluid, alcoholic or non-alcoholic drink or a precursor thereof, a bioreactor, food, environmental sample, plant or seed material, hereditary material, bacteria, virus or other biological sample.

7. Method as claimed in claim 1, wherein the oxidase is selected from glucose oxidase, galactose oxidase, galactose oxidase, bilirubin oxidase, cholesterol oxidase, sarcosine oxidase, xanthine oxidase, amine oxidase, amino acid oxidase, alcohol oxidase pyruvate oxidase, uricase or another oxidase, which enzymatically convert their substrates with formation of hydrogen peroxide.

8. Method as claimed in claim 1, further comprising determining enzyme inhibitors, wherein a reaction-retarding effect of an enzyme inhibitor on the degradation of an enzyme substrate caused by an oxidase with release of hydrogen peroxide is determined with the aid of lanthanoid-ligand complex.

9. Method as claimed in claim 1, further comprising determining enzyme activators, wherein the reaction-accelerating effect of an enzyme activator on the degradation of an enzyme substrate caused by an oxidase with release of hydrogen peroxide is determined with the aid of a lanthanoid-ligand complex.

10. Method as claimed in claim 1, further comprising determining antigens, wherein an oxidase-labelled antibody is used in an immunoanalytical method and, after single or multiple antigen-antibody binding and addition of the enzyme substrate, the hydrogen peroxide that is formed by the oxidase is determined and used to determined the antigen.

11. Method as claimed in claim 9 further comprising the immunohistochemical detection of antigens, wherein an oxidase-labelled antibody binds to an antigen present in a tissue section and the binding site is optically visualized by adding a lanthanoid-ligand complex and an enzyme substrate.

12. Method as claimed in claim 1, further comprising the determination of nucleic acid oligomers, wherein a nucleic acid single strand is labeled with an oxidase and, after hybridization and after addition of enzyme substrate, its activity is detected optically by means of the generated hydrogen peroxide and is used to determine a nucleic acid sequence.

13. Method as claimed in claim 3, wherein the oxidase, the oxidase-labelled antibody or the oxidase-labelled oligomer and/or the lanthanoid-ligand complex is present in an immobilized form on or in a particle, on a planar element, on a light wave guide or on or in a polymer matrix.

14. Method as claimed in claim 13, wherein the polymer matrix consists of a hydrogel permeable to hydrogen peroxide and is present in a 0.1 to 10 μm thick layer and is used as a biosensor in single-use tests or is used several times in succession.

15. Method as claimed in claim 3, wherein oxidase, oxidase-labelled antibody or oxidase-labelled oligomer and/or the lanthanoid-ligand complex are present in a microtitre plate in a dissolved or immobilized form and the changes in the optical properties of the lanthanoid-ligand complex are detected or quantitatively determined with the aid of fluorescent imaging methods.

16. Method as claimed in claim 1, wherein a flow system is used in which a sample material, solvent and/or enzymes or enzyme-labelled antibodies or enzyme-labelled oligomers and/or the lanthanoid-ligand complex are transported mechanically.

17. Method as claimed in claim 1, wherein changes in light absorption of the lanthanoid-ligand complex are determined in the wavelength range between 200 and 450 nm.

18. Method as claimed in claim 1, wherein a change in fluorescence of the lanthanoid-ligand complex is determined by irradiating the lanthanoid-ligand complex with light of wavelengths between 300 and 450 nm and a change in the decay time of the emission or the intensity of the emission is measured at wavelengths of more than 500 nm.

19. Method as claimed in claim 1, wherein self-fluorescence of a material or of a system is suppressed by firstly carrying out an excitation impulse and then determining fluorescence of the lanthanoid-ligand complex after a delay phase of 0.1 to 50 us.

20. Method as claimed in claim 1, wherein the formation of hydrogen peroxide is monitored kinetically and concentration of an analyte is determined by means of changes in the light absorption or the fluorescent properties of the lanthanoid-ligand complex that occur per time unit, which changes are caused by the enzymatically generated hydrogen peroxide.

21. Method as claimed in claim 20, wherein the formation of hydrogen peroxide is determined following the change in absorption or fluorescent properties and the analyte is determined by the total change in the light absorption or the fluorescent properties of the lanthanoid-ligand complex that occur.

22. The method of claim 1, wherein said lanthanoid-ligand complex is in a dissolved, solid or immobilized form having the general structure:

$$Ln_x\text{-}Lig_y$$

wherein

Ln is a trivalent ion from the group of lanthanoids, x and y are independently integers from 1 to 20 and the ratio of x:y is 10:1 to 1:3 and Lig is an organic ligand that binds to the lanthanoid ion.

23. The method as claimed in claim 22, wherein Lig has the general structure $R^1\text{—CO—C}(R^2)\text{=C}(X)\text{—}R^3$, wherein no more than two of the residues $R^1$, $R^2$ o $R^3$ can be H, X can be OH, $NHR^4$, $NR^4_2$, $R^1$ to $R^4$ can be H, an alkyl, a cycloalkyl, an alkanoyl, a cycloalkanoyl, an aroyl, $CF_3$, a substituted or non-substituted alkyl residue or alkanoyl residue, OH, $NH_2$, alkylamino or dialkylamino, where each of the residues $R^1$ to $R^4$ can be linked via a substituted or unsubstituted carboxylic or heterocyclic ring to one of the other residues $R^1$ to $R^4$.

24. The method as claimed in claim 22, wherein the lanthanoid is europium, terbium, holomium, dysprosium, lanthanum, erbium or samarium.

25. The method of claim 22, wherein the organic ligand is selected from benzoylacetone, benzoyltrifluoroacetone, dibenzoylmethane, thenoytrifluoroacetone, heterocyclic (ortho-hydroxy)-carboxylic acids, aromatic or heterocyclic ortho-hydroxyketones and derivatives thereof, hydroxyquinones, partially hydrogenated and substituted hydroxyquinone-like compounds, and anellated carbocyclic compounds.

26. The method of claim 25, wherein the anellated carbocyclic compounds are selected from the group consisting of tetracyclines and tetracycline derivatives.

* * * * *

UNITED STATES PATENT AND TRADEMARK OFFICE
CERTIFICATE OF CORRECTION

| | |
|---|---|
| PATENT NO. | : 7,052,864 B2 |
| APPLICATION NO. | : 10/093103 |
| DATED | : May 30, 2006 |
| INVENTOR(S) | : Axel Durkop et al. |

Page 1 of 1

It is certified that error appears in the above-identified patent and that said Letters Patent is hereby corrected as shown below:

On the TITLE page,

[*] Notice: Subject to any disclaimer, the term of this patent is extended or adjusted under 35 USC 154(b) by (456) days Delete the phrase "by 456 days" and insert -- by 406 days--

Signed and Sealed this

Sixteenth Day of January, 2007

JON W. DUDAS
*Director of the United States Patent and Trademark Office*